(12) United States Patent
Ma et al.

(10) Patent No.: US 8,460,638 B2
(45) Date of Patent: Jun. 11, 2013

(54) METHOD OF IMAGING WITH FLUORESCENT MICROSPHERES

(75) Inventors: Guanghui Ma, Beijing (CN); Zhiguo Su, Beijing (CN); Wei Wei, Beijing (CN); Lianyan Wang, Beijing (CN); Qiang Wei, Beijing (CN)

(73) Assignee: Institute of Process Engineering, Chinese Academy od Science, Beijing (CN)

( * ) Notice: Subject to any disclaimer, the term of this patent is extended or adjusted under 35 U.S.C. 154(b) by 788 days.

(21) Appl. No.: 12/441,894

(22) PCT Filed: Sep. 13, 2007

(86) PCT No.: PCT/CN2007/002713
§ 371 (c)(1),
(2), (4) Date: Feb. 9, 2010

(87) PCT Pub. No.: WO2008/043255
PCT Pub. Date: Apr. 17, 2008

(65) Prior Publication Data
US 2010/0143259 A1    Jun. 10, 2010

(30) Foreign Application Priority Data

Sep. 18, 2006    (CN) .......................... 2006 1 0152191

(51) Int. Cl.
*A61B 5/00*    (2006.01)
(52) U.S. Cl.
USPC ....................................................... 424/9.6
(58) Field of Classification Search
None
See application file for complete search history.

(56) References Cited

U.S. PATENT DOCUMENTS

| 5,840,341 | A | 11/1998 | Watts et al. |
| 6,228,291 | B1 | 5/2001 | Lee et al. |
| 2006/0147539 | A1* | 7/2006 | Sung et al. .................... 424/489 |

FOREIGN PATENT DOCUMENTS

| CN | 1607033 A | 4/2005 |
| CN | 1831080 A | 9/2006 |
| JP | 08-059460 A | 3/1996 |

OTHER PUBLICATIONS

Ding Ming, Shi J, Huangfu L, Gao J. Study on preparation of chitosan microspheres. 1998 Chemical World 12: 636-640. Complete English translation.*

Banerjee T, Mitra S, Kumar Singh A, Kumar Sharma R, Maitra A. Preparation, characterization and biodistribution of ultrafine chitosan nanoparticles. 2002 Int. J. Pharm. 243: 93-105.*
Wang LY, Gu YH, Su ZG, Ma GH. Preparation and improvement of release behavior of chitosan microspheres containing insulin. 2006 Int. J. Pharm. 311: 187-195. Published online Jan 24, 2006.*
Al-Jamal et al. An intrinsically fluorescent dendrimer as a nanoprobe of cell transport. 2006 J. Drug Target. 14: 405-412.*
Wartlick et al. Tumour cell delivery of antisense oligonuciceotides by human serum albumin nanoparticles. 2004 J. Control. Release 96: 483-495.*
Dingming et al., "Research of Preparation of the Chitosan Microsphere", Chemical World, 1998, No. 12, pp. 636-639.
Shao Jian et al., "Chitosan Modified by Vanillin and its Adsorption Property", China Environmental Science, 2000, 20(1): 61-64, Abstract only in English.
Sun et al., "Modification of Chitosan and its Adsorption for Metal Ions", Chemical Research, Mar. 2005, vol. 16, No. 1, pp. 29-31, Abstract only in English.
Jani et al., "The Uptake and Translocation of Latex Nanospheres and Microspheres after Oral Administration to Rats", J. Pharm. Pharmacol., 1989, 41:809-812.
Fitzgerald et al., "A gamma-scintigraphic Evaluation of Microparticulate Ophthalmic Delivery Systems: Liposomes and Nanoparticles", International Journal of Pharmaceutics, 40 (1987) 81-84.
Delie, "Evaluation of Nano- and Microparticle Uptake by the Gastrointestinal Tract", Advanced Drug Delivery Reviews 34 (1998) 221-233.
Mehta et al., "Radiolabelled Microspheres for Evaluation of Peyer's Patch Uptake and Lung Delivery", Pharmaceutical Research: Official Journal of the American Association of Pharmaceutical Scientists, vol. 9, No. 10, Oct. 1992 (Supplement), PDD 7339.

* cited by examiner

*Primary Examiner* — Michael G Hartley
*Assistant Examiner* — Jennifer Lamberski
(74) *Attorney, Agent, or Firm* — Knobbe, Martens, Olson & Bear, LLP

(57) ABSTRACT

A method of fluorescence imaging is disclosed that uses a non-labeled fluorescent microsphere comprising a primary amine polymer, wherein the microsphere does not contain an additional fluorescent substance, and wherein at least one primary amine group in the primary amine polymer has the structure of —N═R—, in which R is a residue after the reaction of an aldehyde-type cross-linking substance, and the other primary amine groups have the structure of —$NH_2$. The fluorescence color of the microspheres can be adjusted by selecting different aldehyde-type cross-linking substances or combinations, and the fluorescence intensity of the microspheres can be controlled not only by the addition of the aldehyde-type cross-linking substances and the time of the cross-linking reaction, but also by adjusting the diameters of the microspheres.

11 Claims, 11 Drawing Sheets

METHOD OF IMAGING WITH FLUORESCENT MICROSPHERES

This application is U.S. National Phase of International Application PCT/CN2007/002713, filed Sep. 13, 2007 designating the U.S., and published in Chinese as WO 2008/043255 on Apr. 17, 2008, which claims priority to China Patent Application No. 200610152191.9, filed Sep. 18, 2006.

FIELD OF THE INVENTION

The present invention relates to fluorescent microspheres and the preparation method thereof, as well as their uses as tracers and fluorescent standard calibration products.

BACKGROUND ART

The existing microsphere tracers are mainly prepared by taking polystyrene as raw material and have the disadvantages of poor biocompatibility and poor in vivo degradability. The specific methods thereof are divided into the following two methods. A method includes embedding radioactive nuclides and the compounds thereof in microspheres to prepare radioactive microspheres. After the radioactive microspheres enter the body, a nuclear detector is used to trace the radioactive microspheres for the different positions, contents and conversions thereof in vivo. This method is complex in operation, great dangerous, and demands high experimental conditions, and additionally, it is unsuitable for oral tracing and intracellular tracing[1-3]. The other method includes embedding fluorescent substances in microspheres to prepare fluorescent microspheres. After the fluorescent microspheres enter the body, a fluorescence microscope is used to observe the distribution situation of the fluorescent microspheres in vivo. However, many fluorescent dyes are not stable sufficiently and will quench gradually in vivo. Additionally, the fluorescent substances adhered on the surface of the microspheres will result in the change of the charges on the surface of the microspheres so as to affect the distribution trends thereof, and therefore, the complexity of the research is increased. Furthermore, the fluorescent substances all have certain toxicity which limits the uses of this kind of tracers[4].

SUMMARY OF THE INVENTION

The inventors of the invention have wondrously found that, during the process of preparing microspheres by an emulsifying & cross-linking method, and when a polymer containing primary amines is cross-linked by taking aldehydes as cross-linking agent, microspheres with the following Schiff base structure can be obtained, wherein the microspheres have an obvious phenomenon of self-fluorescence, and by adjusting different preparation processes, the fluorescence color and intensity of the obtained fluorescent microspheres are different respectively.

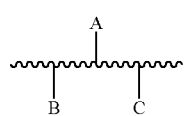

wherein, groups A, B and C are linked to hydrocarbon chain " 〰 " (in the invention, the symbol " 〰 " is used to indicate hydrocarbon chain (that is, the under line in the above formula) and the length of the symbol itself has no limitative meaning on the length of the hydrocarbon chain), and at least one of A, B and C has the structure of —N=R—, in which R is a residue after the reaction of an aldehyde-type cross-linking substance, and the others are —NH$_2$ structure.

The hydrocarbon chain as described in the invention refers to polymer chain which can includes secondary amines, tertiary amines, mercaptoethers, saccharide ring units, aromatic groups, paraffins and olefins. The polymer containing primary amines is preferably selected from a group consisting of chitosan, polylysine, polyethylene imine and the derivatives thereof with primary amine groups. The following description takes chitosan as examples, and however, the content thereof is not limited thereto.

In the composition of the chitosan fluorescent microspheres, the following structure is contained:

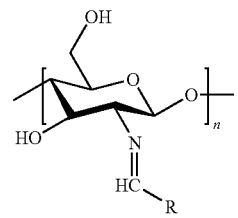

wherein, the

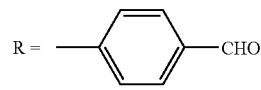

or H, n is an integer of 100-10000. When the cross-linking agent is terephthalic aldehyde,

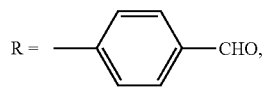

and the microspheres produce bright blue light in the case of being excited by a 365 nm laser; and when the cross-linking agent is formaldehyde, R=H, and the microspheres produce bright red light in the case of being excited by a 543 nm laser.

The fluorescence produced by the fluorescent chitosan microspheres provided in the invention is obviously different from the bright yellow fluorescence produced by the microspheres prepared by taking glutaraldehyde as cross-linking agent in the prior art in the case of being excited by a 488 nm laser.

Another object of the invention is to provide a preparation method of fluorescent microspheres, which includes the steps of:
① mixing a primary amine polymer solution with an oil phase to make a W/O type emulsion;
② adding an aldehyde-type cross-linking agent into the W/O type emulsion to perform a cross-linking reaction so as to obtain solidified microspheres;
③ subjecting the microspheres to centrifugation, washing and collection, and obtaining fluorescent microspheres after drying.

In the preparation method provided in the invention, the cross-linking agent is an aldehyde-type substance.

In the preparation method provided in the invention, the fluorescence color of the fluorescent microspheres can be adjusted by selecting different aldehyde-type substances or the combinations thereof. When the cross-linking agent is terephthalic aldehyde, the microspheres produce bright blue light in the case of being excited by a 365 nm laser; and when the cross-linking agent is formaldehyde, the microspheres produce bright red light in the case of being excited by a 543 nm laser; when the cross-linking agent is glutaraldehyde, the microspheres produce bright yellow light in the case of being excited by a 488 nm laser; and after reduction reaction, the yellow fluorescent microspheres can further produce bright blue light in the case of being excited by a 365 nm laser.

In the preparation method provided in the invention, the fluorescence intensity of the microspheres can be controlled by the addition of the cross-linking agent and the cross-linking time: when the additions of the cross-linking agent are different, the relation between the fluorescence intensity (I) (I) and the concentration of the cross-linking agent (m) is $$I = \frac{I_{max} \cdot m}{k+m};$$

and when the cross-linking times are different, the relation between the fluorescence intensity (I) and the cross-linking time (t) is $$I = \frac{I_{max} \cdot t}{k+t}.$$

In the preparation method provided in the invention, the fluorescence intensity of the microspheres can be controlled by the particle diameter. The fluorescence intensity of the microsphere is directly proportional to the volume of the microsphere.

In the preparation method provided in the invention, in the step ① of the preparation method, the preparation method of the W/O type emulsion is preferably a micropore film emulsification method, that is, making the primary amine polymer solution enter the oil phase through a micropore film under pressure so as to form a W/O type emulsion with uniform particle diameters and controllable sizes, wherein, the micropore film is a SPG (Shirasu Porous Glass) hydrophobic film.

Another object of the invention is to further provide an application of the fluorescent microspheres having the following Schiff base structure in the field of tracers.

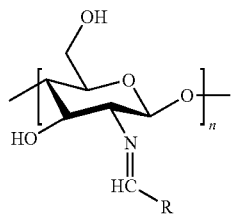

wherein, the number

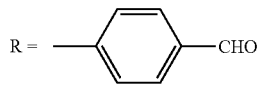

or H, n is an integer of 100-10000.

The microspheres comprising the above Schiff base structure have an obvious phenomenon of self-fluorescence, and the fluorescence output of each microsphere is significantly larger than the fluorescence outputted by the microsphere embedded with fluorescent substances. The microspheres have toleration to light-bleach and the dependency on other environments without modifying the surface property of the microspheres themselves. The color of the fluorescent microspheres can be adjusted by selecting different cross-linking agents or the combinations thereof, and fluorescent microspheres with specific fluorescence intensity can be prepared by controlling the particle diameters of the microspheres and the cross-linking degree. It is the high fluorescence intensity, stable property, uniform sizes and good controllability which makes the fluorescent microspheres can be used to simulate the movement situation of small particles in brain, to trace the situation when particles with different sizes are absorbed through alimentary canal, to detect the influence of different conditions on cytophagy, to trace the process of in vivo metabolic transportation, to trace particles and cells, and to detect the influence of different interfering factors on blood flowing and the influence of different interfering factors on the ingestion and transportation of the microspheres.

Comparing with the prior art, the invention has the following advantages of:

1, the invention discloses the application of the fluorescent microspheres in the field of tracers. The tracer has toleration to light-bleach and the dependency on other environments without modifying the surface property of the microspheres themselves, as well as good biocompatibility and biological degradability.

2, the preparation method of the fluorescent microspheres disclosed in the invention is simple for carrying out. The fluorescence color of the fluorescent microspheres can be adjusted conveniently by selecting different cross-linking agents or the combinations thereof, and fluorescent microspheres with specific fluorescence intensity can be prepared conveniently by controlling the particle diameters of the microspheres and the cross-linking degree.

3, the new primary amine polymer microspheres provided in the invention enlarges the application scope thereof as tracers and fluorescent calibration products.

SPECIFIC MODE OF CARRYING OUT THIS INVENTION

In order to further explain the spirit of the invention, several examples of the invention will be described below, and however, the content of the invention is not limited thereto.

EXAMPLE 1

The preparation process of a 9.5 μm fluorescent chitosan microspheres taking terephthalic aldehyde as cross-linking agent was as follows: A hydrophobic SPG film with a pore diameter of 9.1 μm was placed into a commercial KP18C (a surfactant, from Shin-Etsu Chemical Co., Ltd) to wet the pores sufficiently. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.21 kgf/cm$^2$, the water phase was pressed into the oil phase through a hydrophobic micropore film with uniform pore diameters to obtain a W/O type emulsion. The obtained emulsion was added slowly with terephthalic aldehyde as cross-linking agent to perform cross-linking at normal temperature. After the cross-linking was completed, the obtained chitosan microspheres was washed with petroleum ether, acetone and ethanol in turn and vacuum dried for 24 hrs, and thereafter, a 9.5 μm final product microspheres with uniform sizes were obtained for standby. The microspheres showed bright blue fluorescence under the excitation of a 365 nm laser.

EXAMPLE 2

Figure 1:
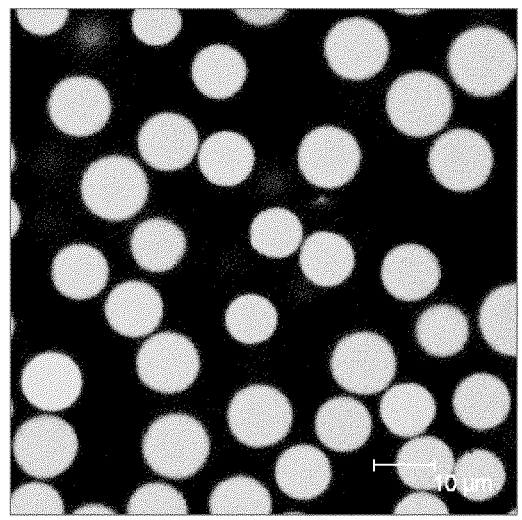
FIG. 1 shows the bright yellow fluorescence produced by the fluorescent chitosan microspheres in the case of being excited by a 488 nm laser when glutaraldehyde is taken as cross-linking agent.

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.21 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent to perform cross-linking at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. The microspheres showed bright yellow fluorescence under the excitation of a 488 nm laser (as shown in FIG. 1).

EXAMPLE 3

The preparation process of a 9.5 μm fluorescent chitosan microspheres taking formaldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.21 kgf/cm$^2$, the water phase was pressed into the oil phase through a hydrophobic micropore film with uniform pore diameters to obtain a W/O type emulsion. The obtained emulsion was added slowly with formaldehyde as cross-linking agent to perform cross-linking at normal temperature. After the cross-linking was completed, the obtained chitosan microspheres was washed with petroleum ether, acetone and ethanol in turn and vacuum dried for 24 h, and thereafter, a 9.5 μm final product microspheres with uniform sizes were obtained for standby. The microspheres showed bright red light under the excitation of a 543 nm laser.

EXAMPLE 4

The preparation process of a 9.6 μm fluorescent polylysine microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of polylysine to make the concentration thereof to be 1 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.41 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent to perform cross-linking at normal temperature. After the cross-linking was completed, the obtained chitosan microspheres were washed with petroleum ether, acetone and ethanol in turn and vacuum dried for 24 h, and thereafter, a 9.6 μm final product microspheres with uniform sizes were obtained for standby. The microspheres showed bright yellow fluorescence under the excitation of a 488 nm laser.

EXAMPLE 5

The preparation process of a 9.5 μm fluorescent chitosan microspheres by taking NaBH$_4$ as reducing agent and taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.21 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent to perform cross-linking at normal temperature. After the cross-linking was completed, the obtained chitosan microspheres was washed with petroleum ether, acetone and ethanol in turn and vacuum dried for 24 h, and thereafter, a 9.5 μm microspheres with uniform sizes were obtained for standby. The prepared microspheres were reduced for 24 h in a 0.1 M NaOH aqueous solution with 1% NaBH$_4$ at room temperature, and a 9.5 μm final product microspheres were obtained after centrifugal drying. The microspheres showed bright blue fluorescence under the excitation of a 365 nm laser.

EXAMPLE 6

The preparation process of a 2.8 μm fluorescent chitosan microspheres taking glutaraldehyde as cross-linking agent was as follows: A hydrophobic SPG film with a pore diameter of 2.8 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 2.8 μm final product microspheres with uniform sizes were obtained for standby. By flow detection, the microspheres had a fluorescence intensity of 42.2 at FL1-H channel and a fluorescence intensity of 27.4 at FL2-H channel.

EXAMPLE 7

The preparation process of a 5.7 μm fluorescent chitosan microspheres taking glutaraldehyde as cross-linking agent was as follows: A hydrophobic SPG film with a pore diameter of 5.4 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 5.7 μm final product microspheres with uniform sizes were obtained for standby. By flow detection, the microspheres had a fluorescence intensity of 299.2 at FL1-H channel and a fluorescence intensity of 192.7 at FL2-H channel.

EXAMPLE 8

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 982.2 at FL1-H channel and a fluorescence intensity of 784.4 at FL2-H channel.

EXAMPLE 9

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 30 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 192.3 at FL 1-H channel.

EXAMPLE 10

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 311.2 at FL 1-H channel.

EXAMPLE 11

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 90 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 337.6 at FL1-H channel.

EXAMPLE 12

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm$^2$, the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=0.5:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 245.2 at FL 1-H channel.

EXAMPLE 13

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm², the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 346.9 at FL1-H channel.

EXAMPLE 14

The preparation process of a 9.5 μm fluorescent chitosan microspheres taking glutaraldehyde as cross-linking agent was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.97 kgf/cm², the water phase was pressed into the oil phase through a hydrophobic micropore film with uniform pore diameters to obtain a W/O type emulsion. The obtained emulsion was added slowly with glutaraldehyde as cross-linking agent (aldehyde group amount:amino group amount=1.5:1) to perform cross-linking for 60 minutes at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. By flow detection, the microspheres had a fluorescence intensity of 392.4 at FL1-H channel.

EXAMPLE 15

Figure 2:
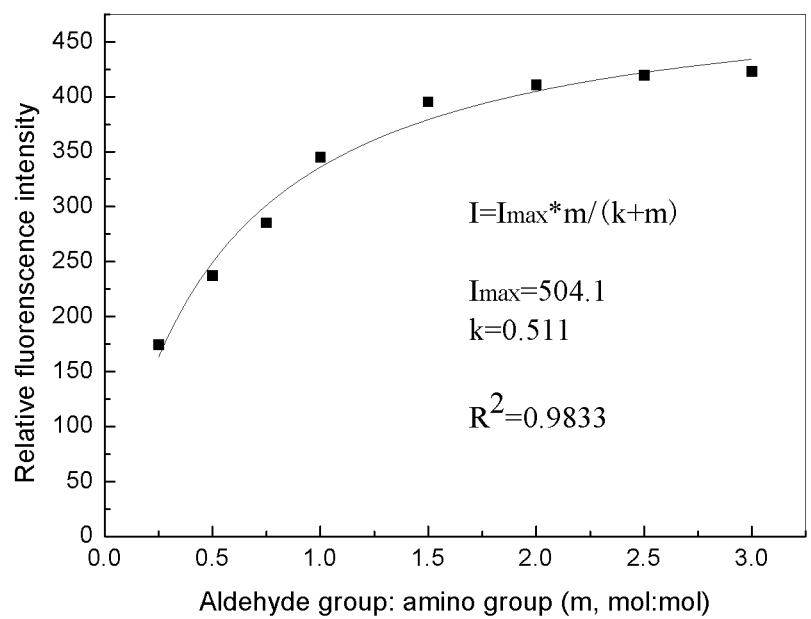
FIG. 2 shows a relation curve of the relative fluorescence intensity and the cross-linking agent addition (indicated by the ratio of aldehyde group/amino group) of the fluorescent chitosan microspheres.

The preparation process of the 9.5 μm fluorescent chitosan microspheres taking glutaraldehyde as cross-linking agent under different cross-linking concentrations was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. A 4 wt % oil soluble emulsifier, that is, PO-500, was added into a mixed phase of liquid paraffin and petroleum ether, and taken as an oil phase after being stirred uniformly. Under a pressure of 0.21 kgf/cm², the water phase was pressed into the oil phase through a hydrophobic micropore film with uniform pore diameters to obtain a W/O type emulsion. The obtained emulsion was added slowly with different amounts of glutaraldehyde as cross-linking agent to perform cross-linking for 1 hour at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. The microspheres were measured by a flow cytometer for the fluorescence intensities of the microspheres under different amounts of cross-linking agent, and as shown in FIG. 2, the relation formula of the fluorescence intensity of the microspheres and the amount of cross-linking agent is $$I = \frac{I_{max} \cdot m}{k + m}.$$

EXAMPLE 16

Figure 3:
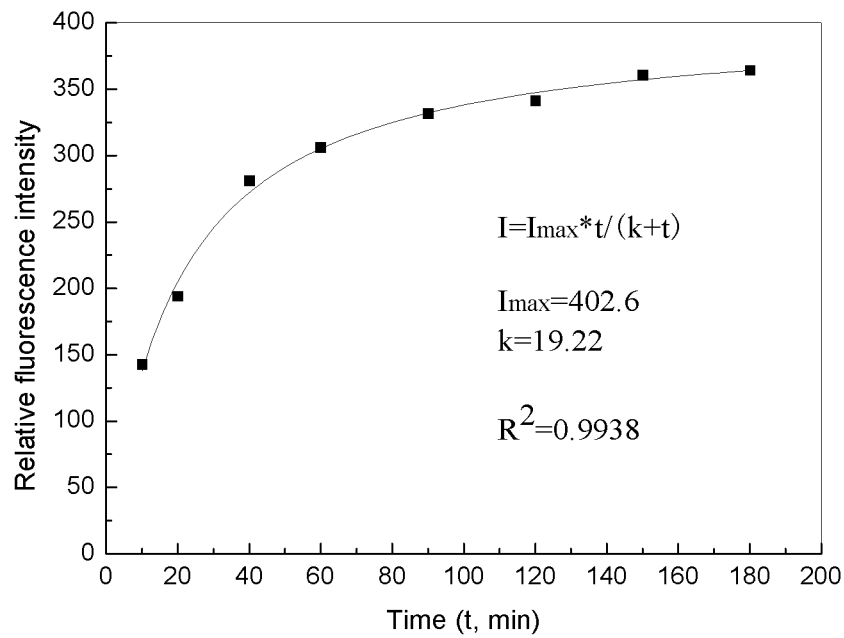
FIG. 3 shows a relation curve of the relative fluorescence intensity and the cross-linking time of the fluorescent chitosan microspheres.

The preparation process of the 9.5 μm fluorescent chitosan microspheres taking glutaraldehyde as cross-linking agent under different cross-linking concentrations was as follows: A hydrophobic SPG film with a pore diameter of 9.1 μm was placed into a commercial KP18C to wet the pores sufficiently so as to ensure that the hydrophobic chains on the film extend completely. A 1 wt % acetic acid aqueous solution was formulated and added with a certain amount of chitosan to make the concentration thereof to be 2 wt %. After the chitosan was dissolved completely, the solution was filtered and taken as a water phase for standby. An oil soluble emulsifier, that is, PO-500, was added into a mixed phase of liquid paraffin and petroleum ether, and taken as an oil phase after being stirred uniformly. Under a pressure of 0.21 kgf/cm², the water phase was pressed into the oil phase through a hydrophobic micropore film with uniform pore diameters to obtain a W/O type emulsion. The obtained emulsion was added slowly with the same amount of glutaraldehyde as cross-linking agent to perform cross-linking for different times at normal temperature. After the cross-linking was completed, the obtained chitosan microspheres were washed with petroleum ether, acetone and ethanol in turn and vacuum dried for 24 h, and thereafter, a 9.5 μm final product microspheres with uniform sizes were obtained for standby. The microspheres were measured by a flow cytometer for the fluorescence intensities of the microspheres under different cross-linking times, and as shown in FIG. 3, the relation formula of the fluorescence intensity of the microspheres and the amount of cross-linking agent is $$I = \frac{I_{max} \cdot t}{k + t}.$$

EXAMPLE 17

Figure 4:
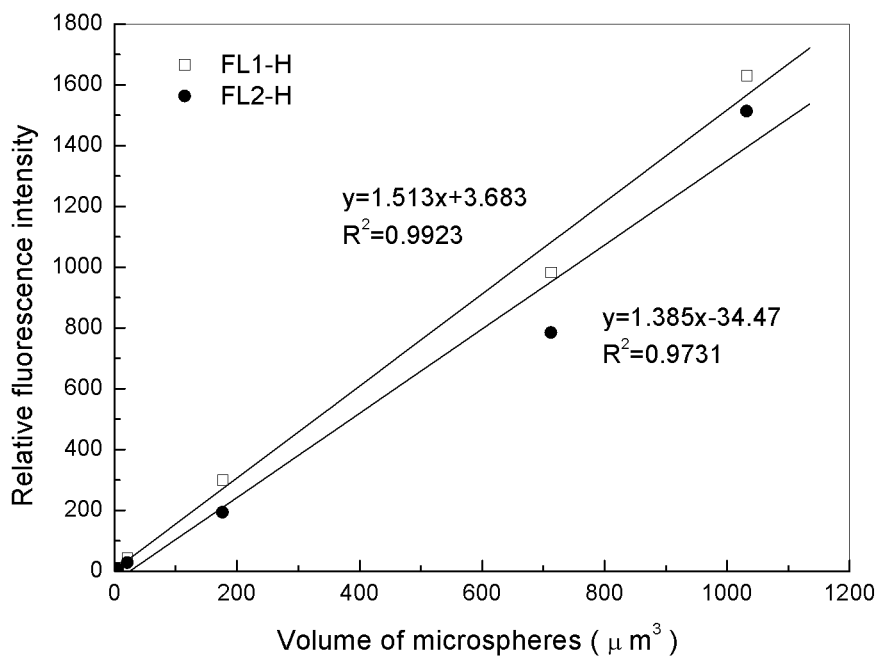
FIG. 4 shows a relation curve of the relative fluorescence intensity and the particle diameter (indicated by the volume of the microsphere) of the fluorescent chitosan microspheres.

Taking glutaraldehyde cross-linking agent as example, the preparation method of fluorescent chitosan microspheres with different particle diameters were the same as those described above except that the pore size of the used films were different, and the prepared fluorescent chitosan microspheres were also different. The fluorescence intensities of the microspheres with different particle diameters were measured by a flow cytometer, and as shown in FIG. 4, there was a good linear relation between the fluorescence intensities and particle diameters of the microspheres.

EXAMPLE 18

Figure 5:
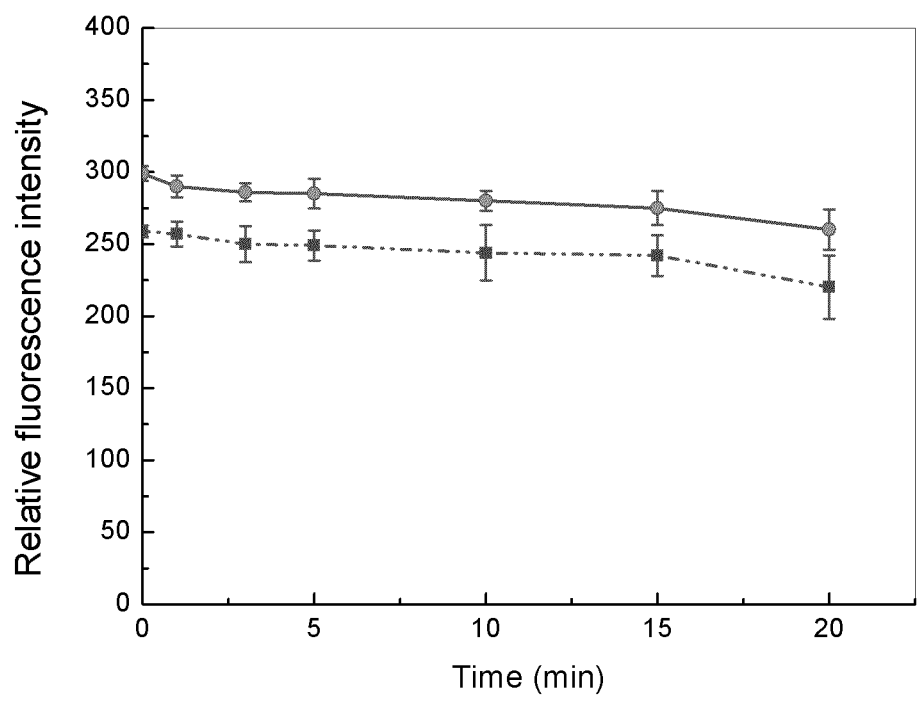
FIG. 5 shows a relation curve of the relative fluorescence intensity and the time of the fluorescent chitosan microspheres (real line) and commercial microspheres (broken line) after being irradiated by strong laser, which reflects the situation of fluorescence quenching.

After the fluorescent chitosan microspheres and commercial microspheres were irradiated by a 2 mw strong laser for different times, the fluorescence intensity changes thereof were measured as shown in FIG. 5. It could be seen that, comparing with the commercial microspheres, the fluorescent chitosan microspheres had the same stability.

EXAMPLE 19

Figure 6:
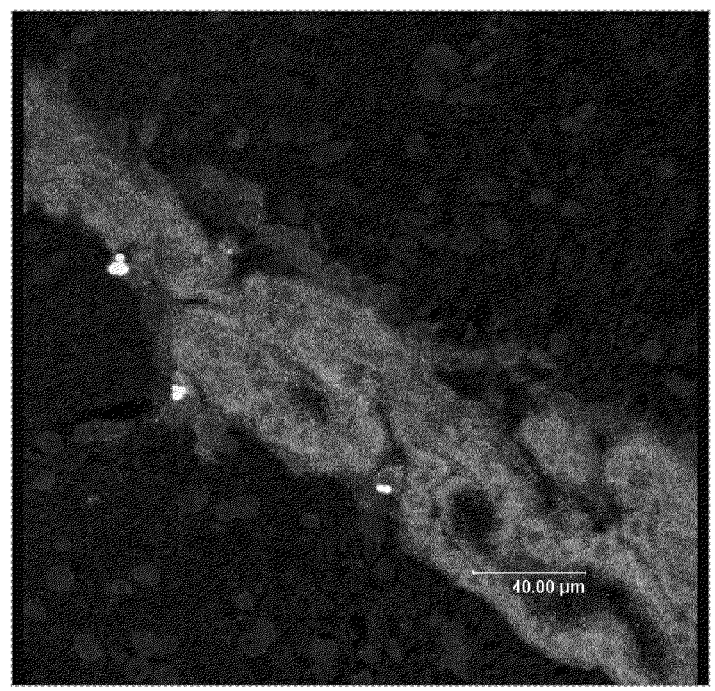
FIG. 6 shows the 1.9 μm fluorescent chitosan microspheres which distribute in the hippocampal particle layer in brain.
Figure 7:
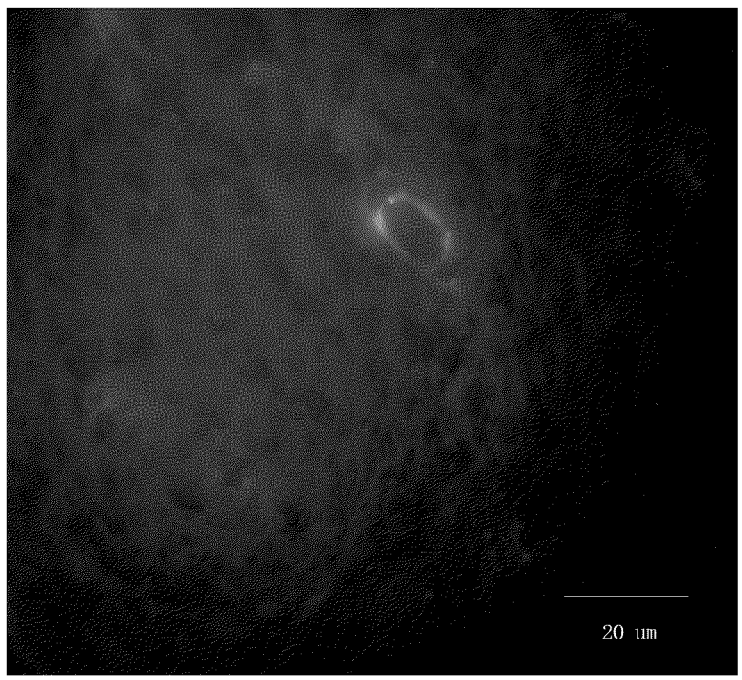
FIG. 7 shows the 1.9 μm fluorescent chitosan microspheres which distribute around the vascular wall in brain.
Figure 8:
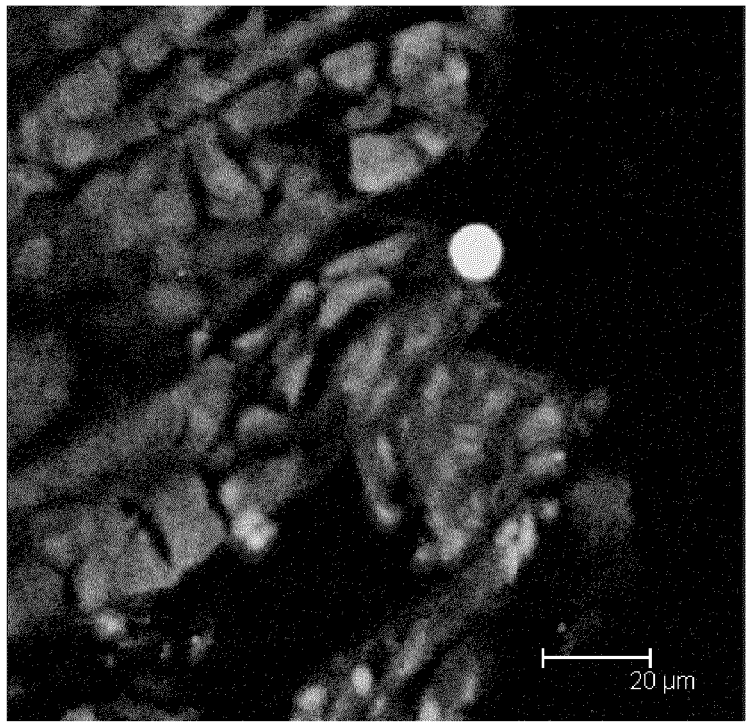
FIG. 8 shows the 7.2 μm fluorescent chitosan microspheres which distribute in stomach.
Figure 9:
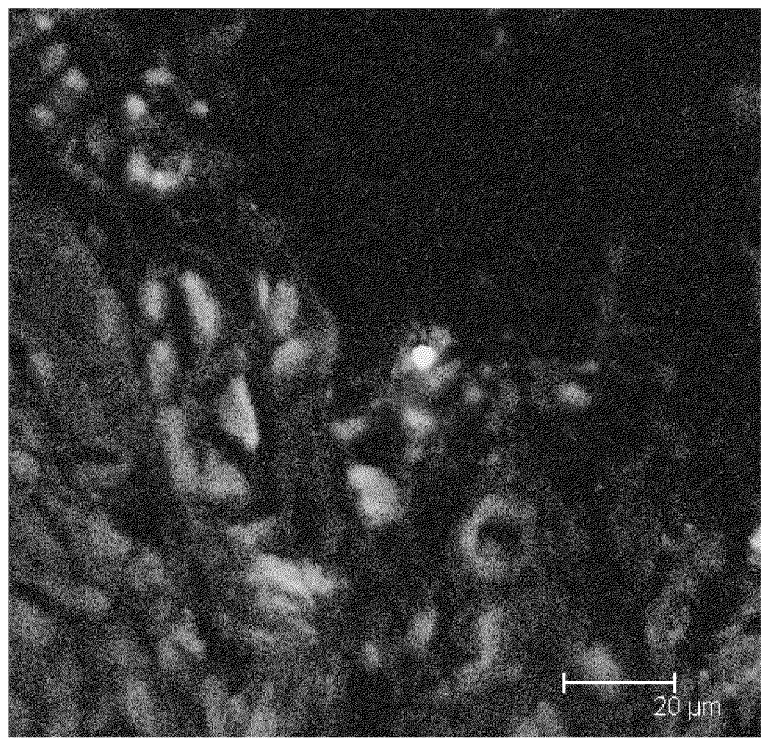
FIG. 9 shows the 2.1 μm fluorescent chitosan microspheres which distribute in stomach.
Figure 10:
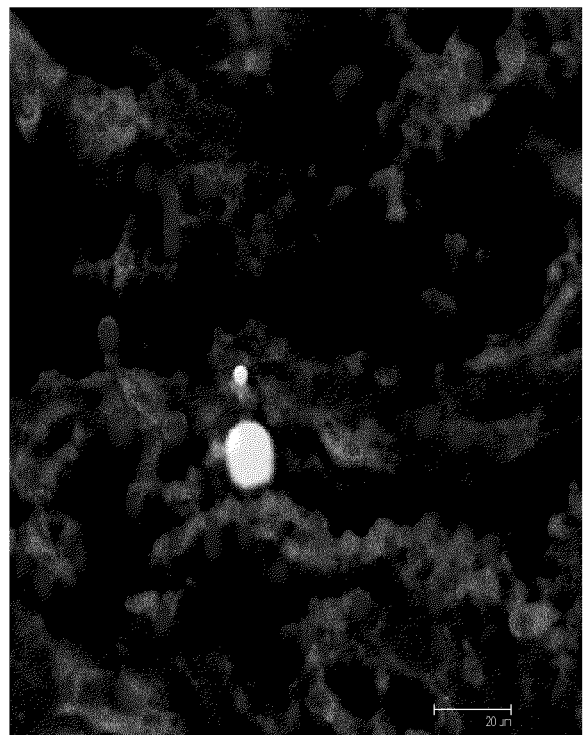
FIG. 10 shows the 2.1 μm and 7.2 μm fluorescent chitosan microspheres which distribute in small intestine.
Figure 11:
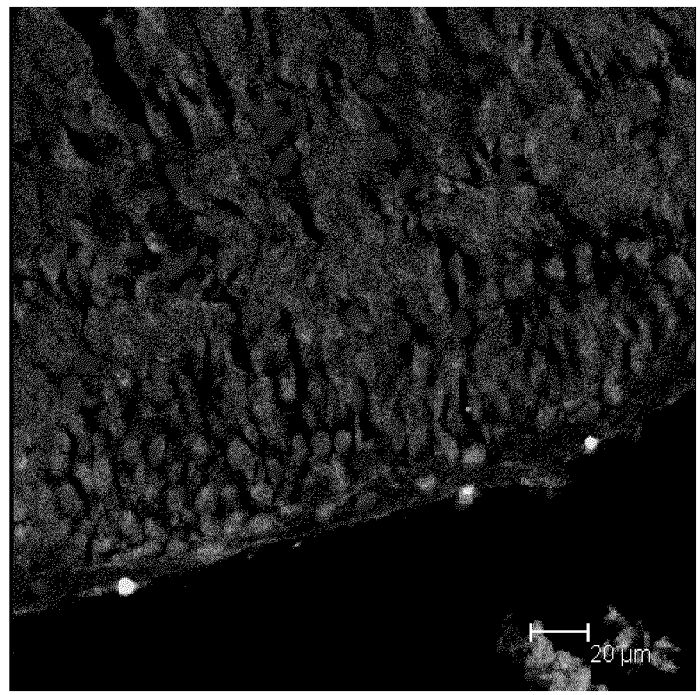
FIG. 11 shows the 2.1 μm fluorescent chitosan microspheres which distribute in colon.
Figure 12:
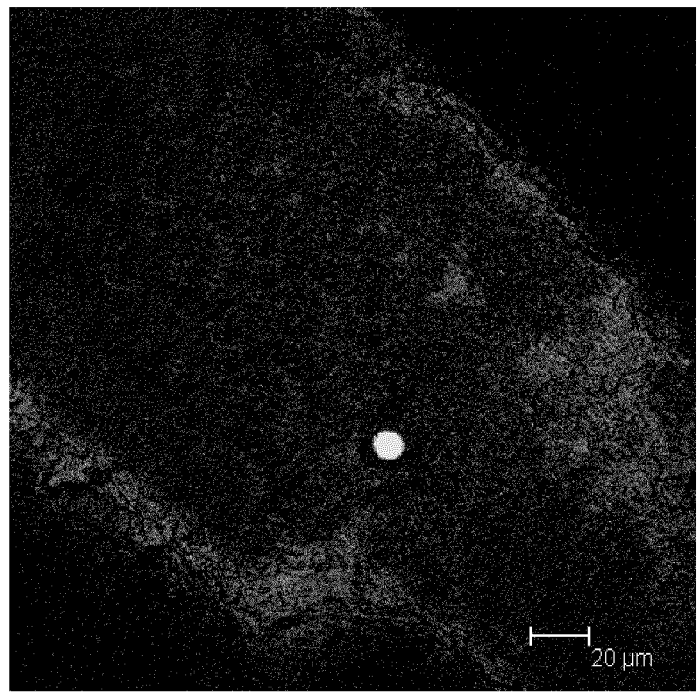
FIG. 12 shows the 7.2 μm fluorescent chitosan microspheres which distribute in blood vessel.
Figure 13:
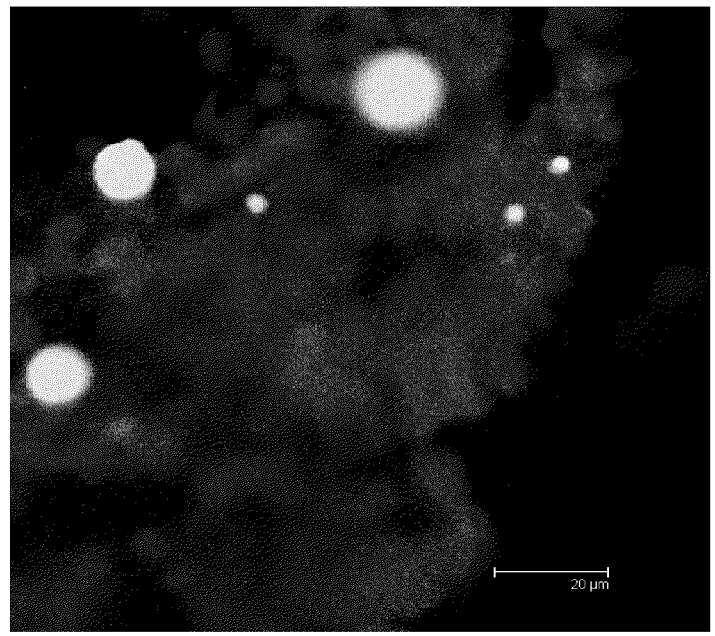
FIG. 13 shows the 2.1 μm and 7.2 μm fluorescent chitosan microspheres which distribute in mesenteric lymph node.
Figure 14:
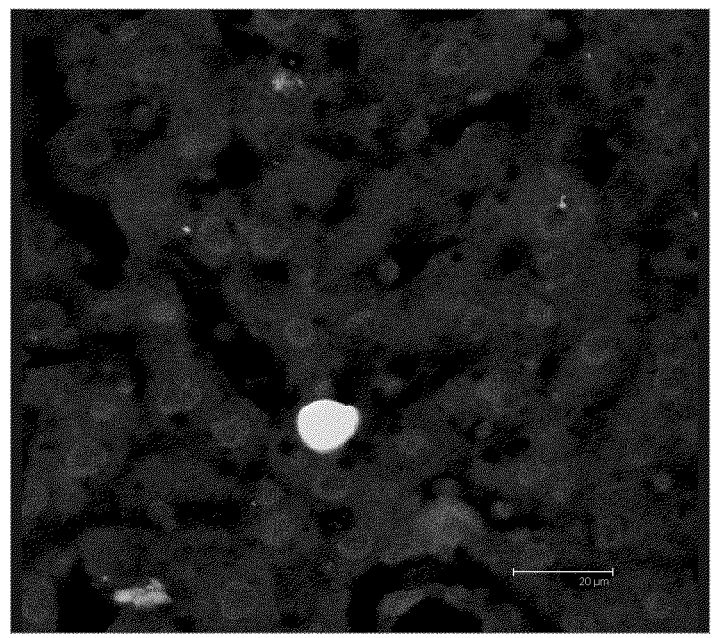
FIG. 14 shows the 7.2 μm fluorescent chitosan microspheres which distribute in liver.
Figure 15:
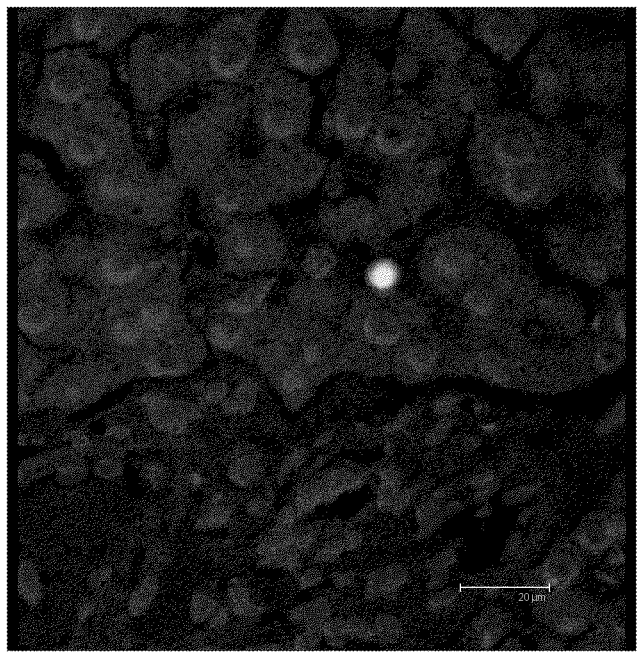
FIG. 15 shows the 2.1 μm fluorescent chitosan microspheres which distribute in liver.
Figure 16:
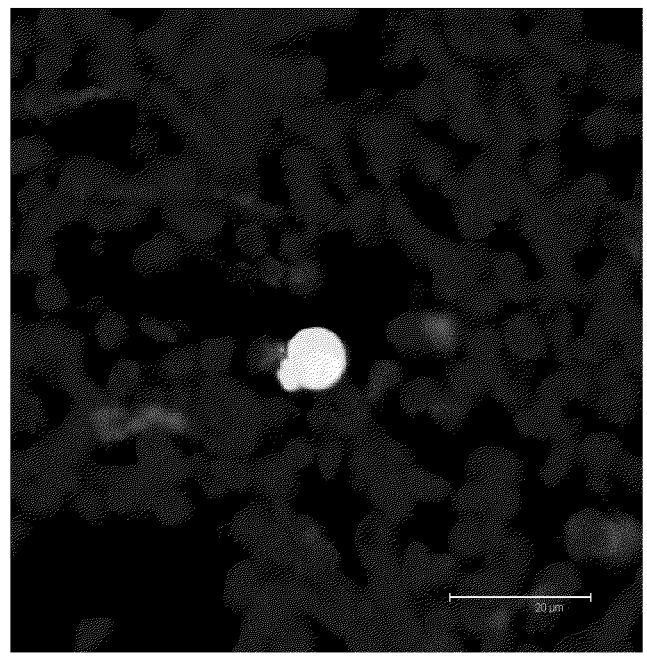
FIG. 16 shows the 7.2 μm fluorescent chitosan microspheres which distribute in spleen.
Figure 17:
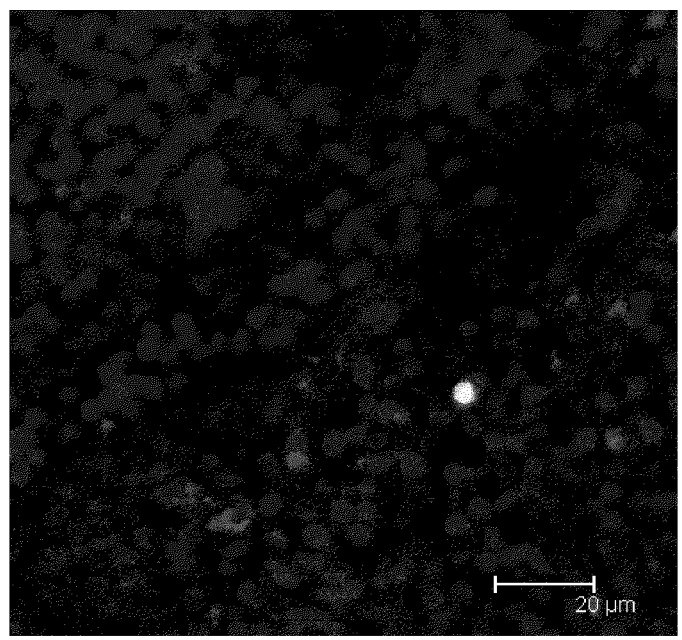
FIG. 17 shows the 2.1 μm fluorescent chitosan microspheres which distribute in spleen.

10 μL of the 1.9 μm microspheres prepared with the above method was extracted and injected into the brain parenchyma of a rat with an injecting amount of $2\times10^6$ by utilizing a brain solid positioner to investigate the movement situation of small particle substances in brain. After 1 day, the brain tissue was extracted and subjected to pathological section and Hoechst stain, and then observed by a laser scanning confocal microscope. It was found that the microspheres were enriched in the hippocampal particle layer of the brain and had a trend of perforating the blood vessel in brain (as shown in FIGS. 6, 7). Thus, it could be seen that the fluorescent chitosan microspheres could be used as the tracer for investigating the movement situation of small particles in the brain of rats.

EXAMPLE 20

Three kinds of microspheres with the sizes of 2.1 μm, 7.2 μm and 12.5 μm as prepared with the above methods were extracted and suspended in water, and then used for performing stomach infusion for a rat with an addition of $2\times10^6$ for each particle diameter and a stomach infusion amount of 1 mL so as to investigate the situation of absorption and distribution of particles with different sizes by the bowel. After 3 days, the stomach, small intestine, colon, mesenteric blood vessel, mesenteric lymph node, liver, skin, muscle, bone, brain, lung, heart and kidney of the rat were extracted and subjected to paraffin pathological section and Hoechst stain, and then observed under a laser scanning confocal microscope so as to determine if the fluorescent chitosan microspheres were distributed in the tissue sections. The results indicated that, the 12.5 μm microspheres were not absorbed, the 7.2 μm microspheres could remain in the stomach and small intestine, and the 2.1 μm microspheres could remain in the stomach, small intestine and colon. For the 7.2 μm and 2.1 μm microspheres, after being absorbed, a part thereof would remain in the mesenteric lymph node, and the other part would reach the liver and spleen through the mesenteric blood vessel and be phagocytosed therein, and furthermore, there was no distribution of microspheres in other tissues (as shown in FIG. 8-17). Thus, it could be seen that the fluorescent chitosan microspheres could be used as the tracer for investigating the size dependency of the intestinal and gastric mucosae on the adherence and ingestion of microparticles, as well as the distribution of microparticles.

EXAMPLE 21

Figure 18:
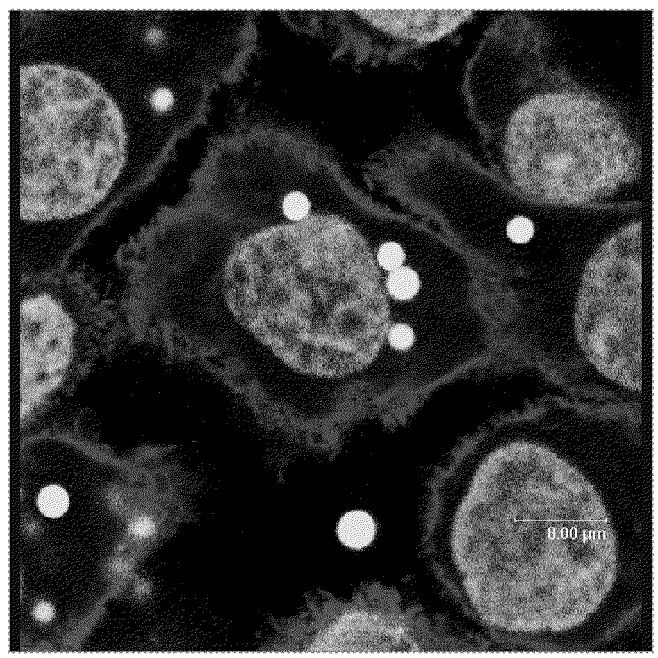
FIG. 18 shows the situation that HepG2 human liver cancer cells phagocytose the 1.9 μm fluorescent chitosan microspheres at 4° C.
Figure 19:
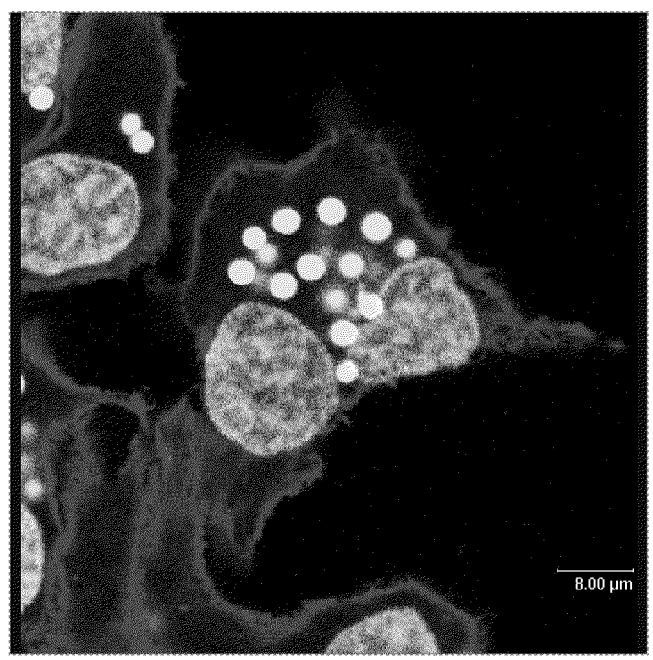
FIG. 19 shows the situation that HepG2 human liver cancer cells phagocytose the 1.9 μm fluorescent chitosan microspheres at 37° C.
Figure 20:
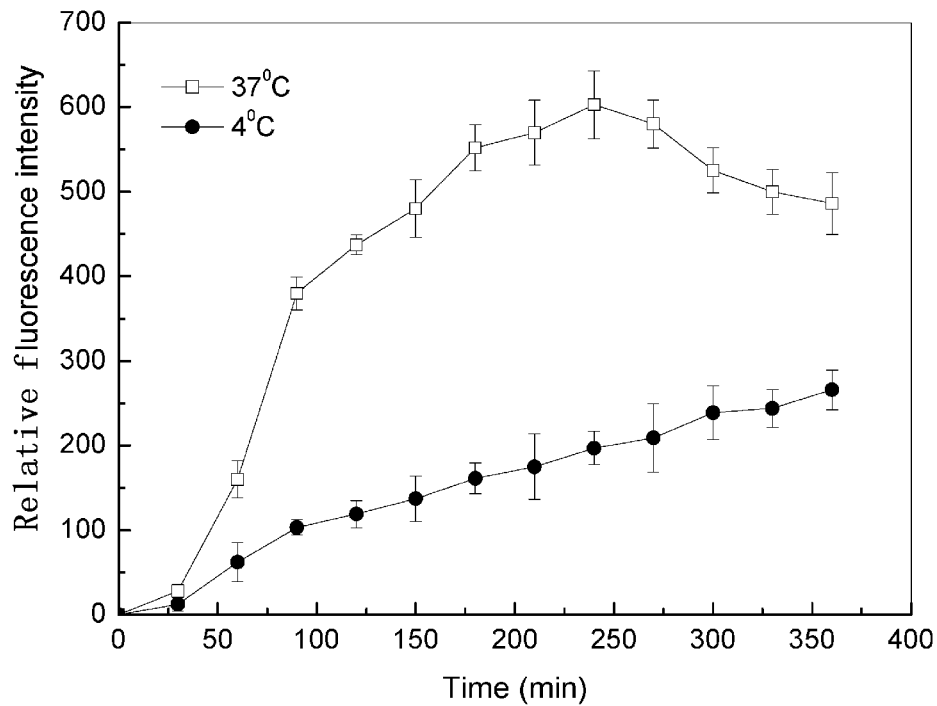
FIG. 20 shows a time dependent curve of the fluorescence intensity of the 1.9 μm fluorescent chitosan microspheres phagocytosed by HepG2 human liver cancer cells under different temperatures.

The 1.9 μm microspheres with a concentration of $2\times10^5$/mL as prepared with the above method was co-cultured with HepG2 human liver cancer cells for 6 h and then subjected to Rhodamine-phalloidin and Hoechst fixed stain, and thereafter, observed for the situation that the microspheres were phagocytosed by the cells under different temperatures under a laser scanning confocal microscope (as shown in FIGS. 18, 19); the dynamics of the situation that the microspheres were phagocytosed by the cells under different temperatures was investigated by a flow cytometer (as shown in FIG. 20). The results indicated that, the phagocytosis ability at 37° C. was larger than that at 4° C., and additionally, an outward discharging effect would appear in the case of saturation. Thus, it could be seen that the fluorescent chitosan microspheres could be used as the tracer for investigating the influence of temperature on the phagocytosis of the fluorescent chitosan microspheres by the HepG2 human liver cancer cells.

EXAMPLE 22

The 6.8 μm microspheres as prepared with the above method was injected into any part in the circulating system of a rat. These microspheres would finally accumulate in capillary vessels and could be counted at a blood vessel which had been cut open by a fluorescence spectrophotometer, a fluorescence micropore plate or a flow cytometer. Because the amount of the microspheres is directly proportional to the blood flow, the magnitude of the blood flow at a specific position could be measured by detecting the fluorescence intensity of the microspheres at the position. After a treatment of tissue section, the fluorescence could be maintained and further observed in morphology by a laser scanning confocal microscope so as to obtain a fluorescence image. Thus, it could be seen that the chitosan Schiff base microspheres could be used as the tracer for investigating the situation of local blood flowing. Similarly, the method could further be used for detecting the situation of blood flowing in the organs of kidney, spleen, heart, teeth and the like except that the chitosan fluorescent microspheres with adequate sizes should be selected according to the diameters of the blood vessels; the smaller chitosan fluorescent microspheres (0.5 μm) could be used to trace the occurrence of new blood vessels and had important meaning for researching the occurrence of tumor blood vessels and the continuity of micro-blood vessels.

EXAMPLE 23

Figure 21:
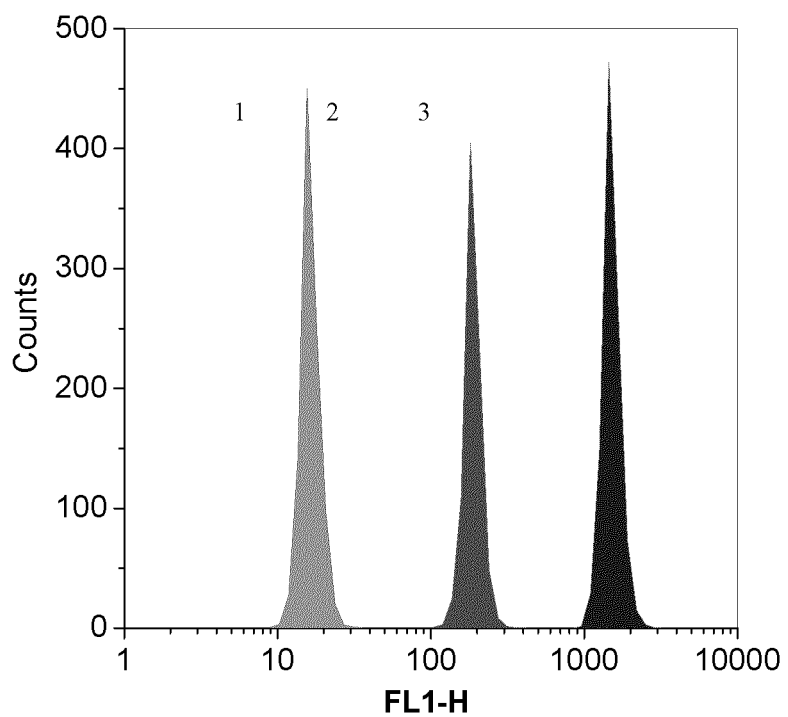
FIG. 21 shows the signals obtained after detecting the 2.0 um (1), 4.7 um (2) and 9.5 um (3) standard finished product microspheres through a flow cytometer.

The preparation processes of the fluorescent chitosan microspheres with different particle diameters were shown in the above examples. The 2.0 μm, 4.7 μm and 9.5 μm uniform fluorescent microspheres being final products were subjected to detection on a flow cytometer and the obtained result was shown in FIG. 21. The microspheres had uniform particle diameters, sharp signal peaks and controllable fluorescence intensity, and therefore they could be used as the standard calibration products for the fluorescence apparatuses of flow cytometer and the like.

References

1 Jani, P., Haklbert, G W., Langridge, J. & Florence, A. T. The uptake of nanoparticles of latex nanospheres and microspheres after oral administration to rats. *J. Pharm. Pharmacol.* 41, 809-812 (1989).

2. Fitzgerald, P., Hadgraft, J., Kreuter, J., & Wilson, C. G. A gamma-scintigraphic evaluation of microparticulate ophtalmic delivery systems: liposome and nanoparticles, *Int. J. Pharm.* 40, 81-84 (1987).

3. Metha, R. C. et al. Radiolabeled microspheres for evaluation of Peyer's patch uptake and lung delivery, *Pharm. Res.* 9, S253 (1992).

4. Delie, F. Evaluation of nano- and microparticle uptake by the gastrointestinal tract. *Adv. Drug Deliv. Rev.* 34, 221-233 (1998).

The invention claimed is:

1. A method of fluorescence imaging a mammal comprising:
administering to the mammal an effective amount of a non-labeled fluorescent microsphere comprising a primary amine polymer, wherein the microsphere does not contain an additional fluorescent substance, and wherein at least one primary amine group in the primary amine polymer has the structure of —N=R—, in which R is a residue after the reaction of an aldehyde-type cross-linking substance, and the other primary amine groups have the structure of —NH$_2$; and imaging fluorescence from said microspheres; and wherein the non-labeled fluorescent microsphere is produced according to a method, comprising:

mixing a solution of the primary amine polymer with an oil phase to make a W/O type emulsion;

adding a cross-linking agent into the W/O type emulsion to perform a cross-linking reaction so as to obtain solidified microspheres; and subjecting the solidified microspheres to centrifugation washing and collection, and obtaining the non-labeled fluorescent microspheres after drying, wherein the cross-linking agent is an aldehyde-type cross-linking substance and the primary amine polymer is chitosan or polylysine.

2. The method according to claim 1, wherein the method of fluorescence imaging provides an image of a condition selected from the group consisting of fluid movement, distribution, biological sample structure, endocytosis, exocytosis, phagocytosis, blood circulation, and any combinations thereof.

3. The method according to claim 1, wherein the primary amine polymer is chitosan.

4. The method according to claim 1, wherein the aldehyde-type cross-linking substance is one or more selected from the group consisting of terephthalic aldehyde and formaldehyde.

5. The method according to claim 1, wherein the aldehyde-type cross-linking substance is glutaraldehyde.

6. The method according to claim 5, wherein the method for producing the non-labeled fluorescent microsphere further comprises subjecting the microspheres obtained after the cross-linking reaction to reduction by a reducing agent.

7. The method according to claim 6, wherein the reducing agent is a borohydride.

8. The method according to claim 3, wherein the method for producing the non-labeled fluorescent microsphere further comprises obtaining a desired fluorescence intensity of the non-labeled fluorescent microsphere by controlling at least one factor selected from the group consisting of the kind of the aldehyde-type cross-linking substances, the addition amount of the aldehyde-type cross-linking substances, and the time of the cross-linking reaction.

9. The method according to claim 3, wherein the method for producing the non-labeled fluorescent microsphere further comprises adjusting the diameter of the non-labeled fluorescent microsphere to obtain a desired fluorescence intensity of the non-labeled fluorescent microsphere.

10. The method according to claim 1, wherein said mixing comprises making the primary amine polymer solution enter the oil phase through a micropore film under pressure.

11. The method according to claim 10, wherein the micropore film is an SPG hydrophobic film.

* * * * *